United States Patent [19]

Sitar et al.

[11] Patent Number: 4,816,024
[45] Date of Patent: Mar. 28, 1989

[54] MEDICAL DEVICE

[75] Inventors: Dennis L. Sitar, Trabuco Canyon; Jean M. Bonaldo, Upland, both of Calif.

[73] Assignee: ICU Medical, Inc., Mission Viejo, Calif.

[21] Appl. No.: 37,325

[22] Filed: Apr. 13, 1987

[51] Int. Cl.$^4$ .............................................. A61M 5/32
[52] U.S. Cl. ..................................... 604/192; 604/263
[58] Field of Search ............... 604/192, 187, 263, 240, 604/241

[56] References Cited

U.S. PATENT DOCUMENTS

| | | |
|---|---|---|
| 2,571,653 | 10/1951 | Bastien . |
| 2,737,948 | 3/1956 | Brown ................................... 604/192 |
| 2,925,083 | 2/1960 | Craig . |
| 3,073,307 | 1/1963 | Stevens ................................ 604/192 |
| 3,134,380 | 5/1964 | Armao . |
| 3,356,089 | 12/1967 | Francis . |
| 3,380,448 | 4/1968 | Sadove et al. . |
| 3,406,687 | 10/1968 | Moyer . |
| 3,658,061 | 4/1972 | Hall . |
| 3,890,971 | 6/1975 | Leeson et al. . |
| 3,943,927 | 3/1976 | Norgren . |
| 3,967,621 | 7/1976 | Schwarz .............................. 604/192 |
| 3,989,044 | 11/1976 | Meierhoefer ....................... 604/192 |
| 4,009,716 | 3/1977 | Cohen ................................. 604/192 |
| 4,026,287 | 5/1977 | Haller . |
| 4,170,993 | 10/1979 | Alvarez . |
| 4,329,989 | 5/1982 | Dallons et al. . |
| 4,373,526 | 2/1983 | Kling . |
| 4,425,120 | 1/1984 | Sampson et al. . |
| 4,507,117 | 3/1985 | Vining et al. . |
| 4,553,962 | 11/1985 | Brunet . |
| 4,631,057 | 12/1986 | Mitchell . |
| 4,737,144 | 4/1988 | Chokai . |

FOREIGN PATENT DOCUMENTS 689751 6/1964 Canada .
1541417 10/1968 France .

Primary Examiner—John D. Yasko
Attorney, Agent, or Firm—Knobbe, Martens, Olson & Bear

[57] ABSTRACT

Disclosed is an improved medical device of the type where a needle is protected by a guard member moved axially along the needle shaft to a permanently locked position. The improvement is the use of an elongated stem member extending from the locking element covering a substantial portion an essentially fail-safe bond between the locking element and the needle and to facilitate manufacture of the device.

18 Claims, 3 Drawing Sheets

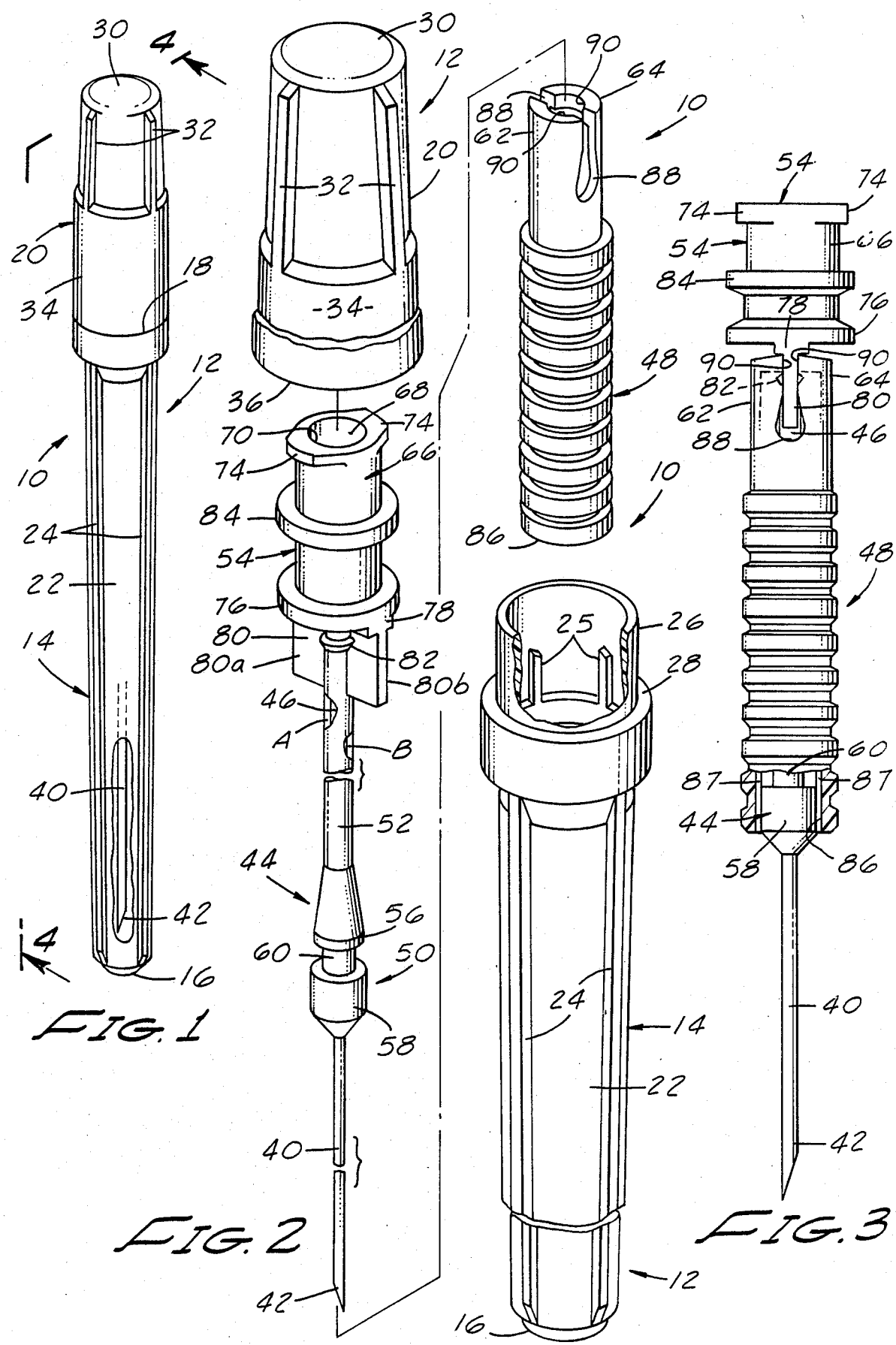

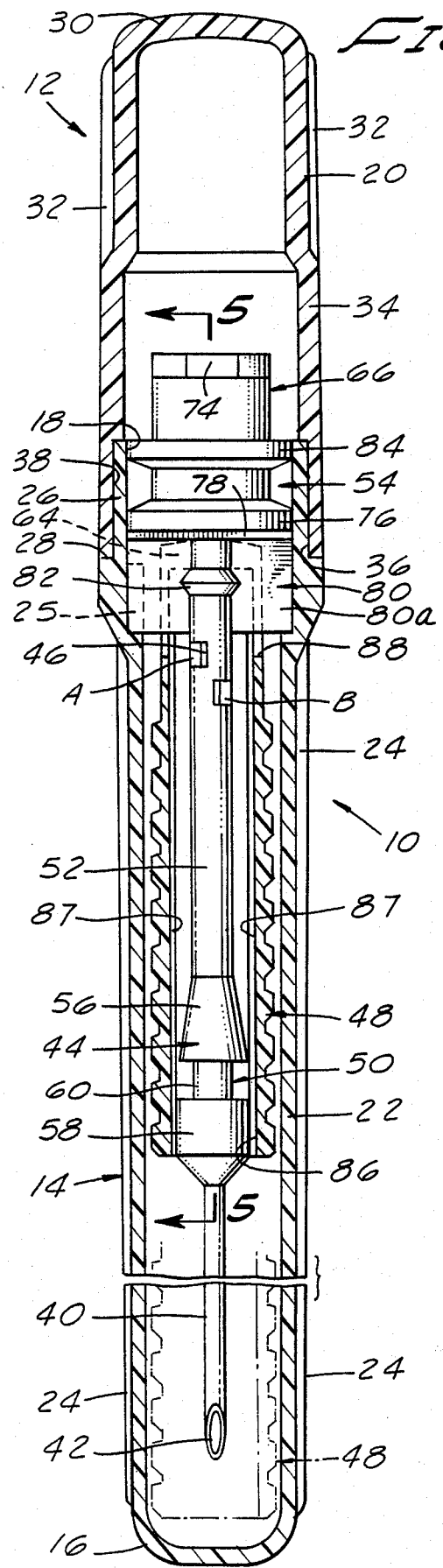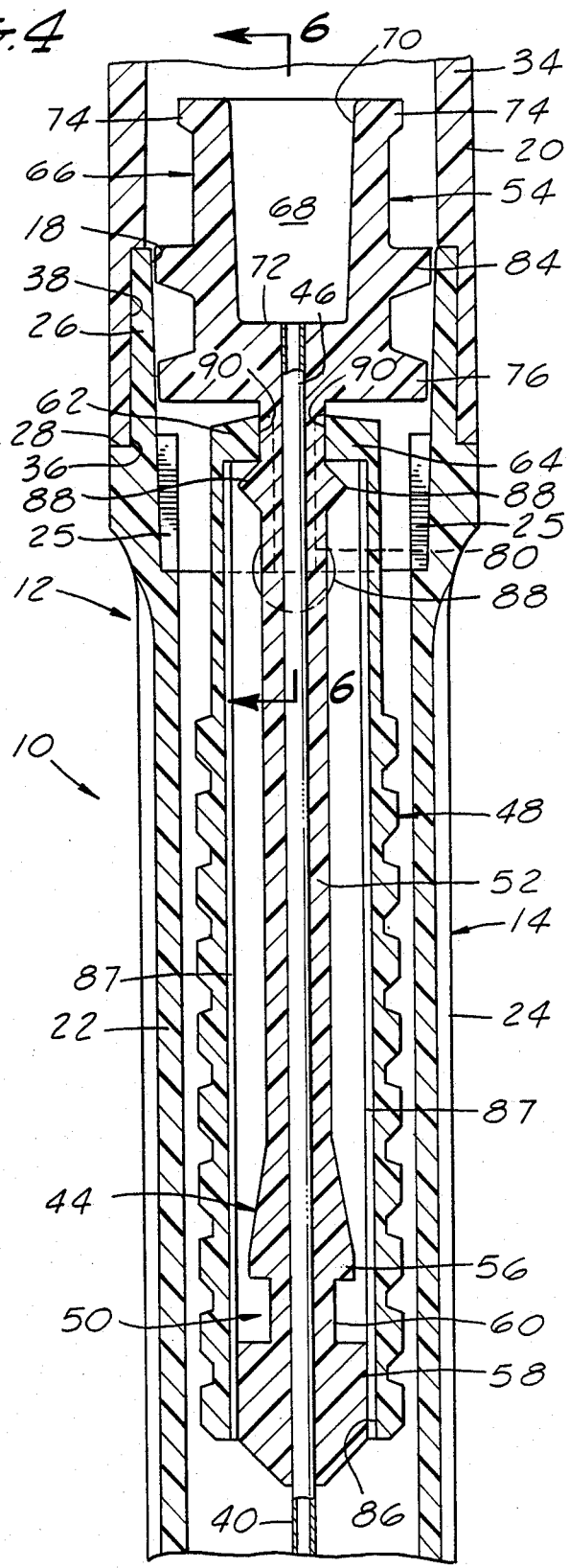

MEDICAL DEVICE

BACKGROUND OF THE INVENTION

1. Field of the Invention

This invention relates to a medical device employing a needle having a guard member which permanently locks in place to protect against accidental needle sticks after the needle has been used. More particularly, it relates to an improved locking element to hold the guard securely in the locked position.

2. Background Discussion

In U.S. patent application Ser. No. 06/849,148, filed Apr. 7, 1986, entitled MEDICAL DEVICE, and U.S. patent application Ser. No. 07/035,434, filed Apr. 7, 1987, and entitled MEDICAL DEVICE, both of these applications assigned to ICU Medical, Inc., the assignee of this application, there is described medical devices using needles having movable guard members which are locked permanently in position after the needle is used. Both of these applications are incorporated herein by reference. In both of these applications, the locking member is mounted on the needle shaft and it is bonded to the shaft by an adhesive. The locking device includes a recessed portion which serves to capture a wedge-type collar piece integral with one end of the guard member. With the collar piece wedged in the recessed portion, the guard is locked in a permanent position once it has been moved forward to cover the tip of the needle.

The purpose of the guard member is to prevent accidental needle sticks. If, however, the bond between the locking element and the exterior surface of the needle fails, the guard member would move and possibly expose the tip of the needle. Moreover, in mass producing such medical devices, it is both expensive and inconvenient to secure the locking element to the needle by means of an adhesive. Although the medical devices described in the above-identified applications represent a substantial improvement in disposable needles, it is desirable to improve their design so that there would not be an accidental failure of the bond between the locking element and the shaft of the needle and would also enable the devices to be mass produced rapidly and inexpensively.

SUMMARY OF THE INVENTION

The present invention provides an improved medical device of the type described in the above-identified applications employing a novel locking element which is securely bonded to the shaft of the needle and facilitates mass production of these devices. There are several features of this invention, no single one of which is solely responsible for its desirable attributes. Without limiting the scope of this invention, as expressed by the claims, its more prominent features will now be discussed briefly. After considering this discussion, and particularly after reading the section of the application entitled DETAILED DESCRIPTION OF THE PREFERRED EMBODIMENT, one will understand how the features of this invention provide the advantages of ease of manufacture and reliability of the bond between the needle shaft and locking element.

One feature of the present invention is the use of a locking element which has an elongated stem section extending from the recess or locking portion of the element. The metal needle extends through this stem section and is securely pressure-bonded to the stem during molding without using adhesives. In accordance with this invention, a substantial portion of the surface of the exterior of the needle shaft is in contact with and bonded to the stem section. Preferably, over 50% of the surface area of the needle is in contact with stem.

The second feature of this invention is that the stem section, locking element section, and a hub member which carries the guard for the needle are of a unitary structure, being molded from the same polymeric material, preferably a polypropylene which is resistant to gamma radiation used to sterilize the needle. Such a polymeric material is sold by the Himont Corporation of Wilmington, Del. under the trade name Himont PD 626.

The third feature of this invention is that the unitary structure of locking section, stem section, and hub are formed using insert molding techniques where the needle element is held in position in the mold cavity with the polymeric material being forced under high pressure in a molten condition into the mold cavity. The needle element is held firmly in place by pin members which extend into the mold cavity and grasp the shaft of the needle element to prevent the needle from bowing or moving laterally in the cavity of the mold.

The preferred embodiment of this invention illustrating all of its features will now be discussed in detail. This embodiment shows the improved device of this invention in the following drawing.

BRIEF DESCRIPTION OF THE DRAWING

The improved medical device of this invention is illustrated in the drawing, with like numerals indicating like parts, and in which:

FIG. 1 is a perspective view of the improved medical device of this invention contained in a two piece, plastic translucent housing.

FIG. 2 is an exploded perspective view of the improved medical device of this invention.

FIG. 3 is a side elevational view, with sections broken away, showing the novel locking element molded in place on the needle and carrying the guard for the needle.

FIG. 4 is a cross-sectional view taken along line 4—4 of FIG. 1.

FIG. 5 is a cross-sectional view taken along line 5—5 of FIG. 4.

DESCRIPTION OF THE PREFERRED EMBODIMENT

Figure 6:
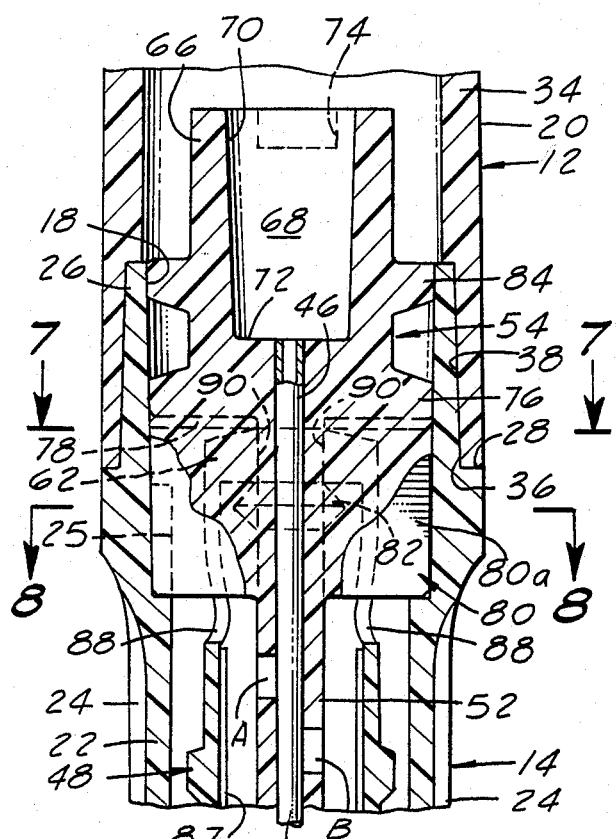
FIG. 6 is a cross-sectional view taken along line 6—6 of FIG. 5.
Figure 7:
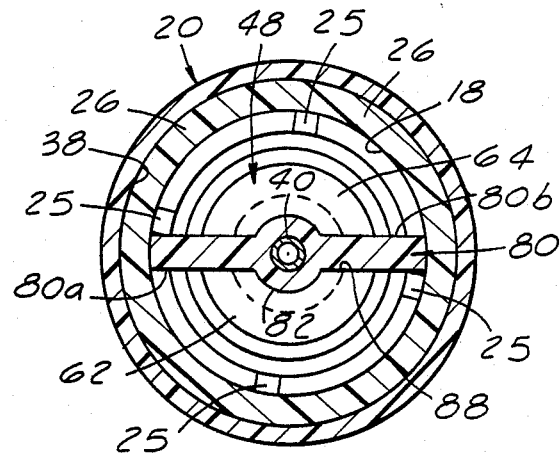
FIG. 7 is a cross-sectional view taken along line 7—7 of FIG. 6.
Figure 8:
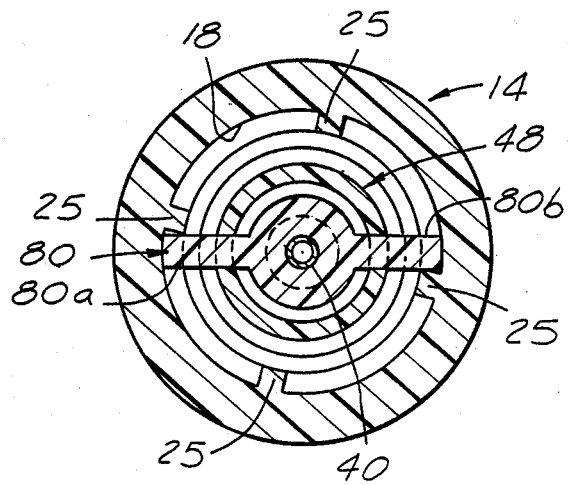
FIG. 8 is a cross-sectional view taken along line 8—8 of FIG. 6.

As best illustrated in FIGS. 1 through 4, the improved medical device 10 of this invention is contained within a housing 12 including a sheath 14 which has a closed end 16, an open end 18 and a cover 20 which fits over the open end of the sheath. The sheath 14 is an elongated member having a generally cylindrical configuration with a side wall 22 that tapers outwardly from the closed end 16 to the open end 18. Running lengthwise along the exterior of the wall 22 are spaced apart splines 24 which facilitate grasping the sheath 14 and turning it. As will be explained hereafter, internal splines 25 facilitate attaching the device 10 to a syringe (not shown). Near the open end 18 of the sheath 14, the side wall 22 flares outwardly and then is formed into an annulus 26 extending upwardly from a ledge 28. The ledge 28 serves as a stop for the cover 20 which fits snugly over the annulus 26. The cover 20 is short relative to the sheath 14 and it has at one end a closed off 30 section surrounded by a series radial ribs 32 which terminate at their internal ends in a wall 34 which defines an open end 36 having an internal offset bore 38 (FIGS. 4–6). The bore 38 mates with the annulus 26 of the sheath 14 when the cover 20 is placed over the sheath.

Within the housing 12 is contained the improved medical device 10, which is sterilized in housing 12 by gamma radiation. The device 10 includes an elongated needle element 40 having a truncated tip 42 at one end and a locking member 44 securely mounted to the other end 46 of the shaft. The locking element 44 carries a guard member 48 which is movable axially along the shaft of the needle element.

Figure 9:
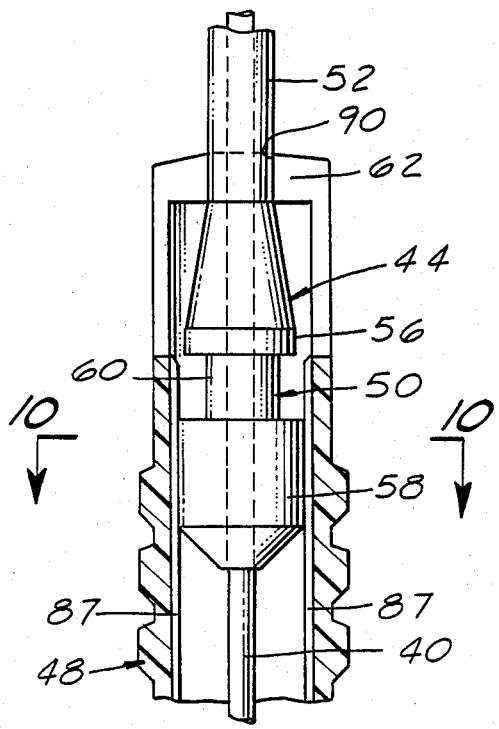
FIG. 9 is a fragmentary view in cross section showing the guard member being moved into locking position.
Figure 10:
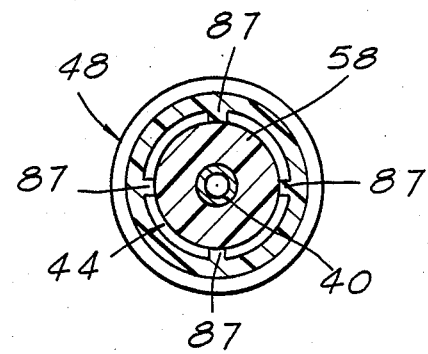
FIG. 10 is a cross-sectional view taken along line 10—10 of FIG. 9.

In accordance with one feature of this invention, the locking element 44 is a unitary structure including a locking section 50, a stem 52, and a hub 54. This locking element 44 is made of any suitable polymeric material and is formed using insert molding techniques where the needle element 40 is held securely in position within a mold cavity having a configuration corresponding to the configuration of the locking element 44. Molten polymer is injected into the mold cavity and a pair of pins (not shown) extend into the cavity and grasp the shaft of the needle element 40 to hold the needle element 40 in position and prevent bowing or lateral movement during formation of the locking element 44. It is highly desirable to hold the needle element 40 with pins because the improved medical device of this invention employs a needle element which is substantially longer than conventional devices. For example, it s two or three times the length of conventional needles used with syringes. This is so because the needle element 40 carries the locking element 44 and the guard member 48 which is movable axially along the shaft between a position where this needle is exposed as shown in FIG. 4 to a locking position where the guard member is moved forward as shown in FIG. 9 to cover the tip 42 of the needle element. After the molten polymeric material is injected into the cavity it cools and shrinks to firmly bond the locking element 44 to the needle shaft. Because a substantial portion of the exterior surface of the needle shaft is in intimate contact with the locking element 44, a secure bond is formed which is highly unlikely to rupture. Thus, the locking element 44 and needle shaft are safely attached to one another so that bond rupture is virtually eliminated. Moreover, the use of costly adhesives in securing the locking element 44 to the needle shaft is eliminated.

The locking element 44 includes a locking section 50 similar to that described in above-identified patent applications and includes a pair of shoulders 56 and 58 separated by an annular recess 60 which captures collar elements 62 and 64 of the guard member 48 when the guard member is moved to the forward position covering the tip 42 of the needle element 40. The stem 52 is essentially an elongated hollow cylindrical member extending between the locking section 50 and the hub 54. The open spaces A and B in the body of the stem result from the pins (not shown) extending into the mold cavity and grasping the needle shaft. The hub 54 includes a connector piece 66 having an internal cavity 68 formed by an inwardly tapering wall 70 which terminates in a generally flat bottom 72. The end 4 of the needle shaft terminates at the bottom 72. At the mouth of the cavity 68 are a pair of dog ears 74 opposed to one another which enable device 10 to be removably attached to a syringe (not shown). An annular platform 76 extends around the base of the hub 54 and it has a block 78 lying lengthwise across its diameter A planar member 80 having generally flat opposing faces 80a and 80b extends outwardly from the exposed side of the block 78. A rib 82 extends around the stem 52 between the faces 80a and 80b of the planar member. This rib 82 is used to hold the guard member 48 in the rearward position where tip 42 of the needle element 40 is exposed. This will be explained in greater detail hereinafter. Between the dog ears 74 and the annular platform 76 is an annular stopper 84 which closes off the open end 18 of the sheath 14 when the device 10 is placed inside the housing 12.

As best illustrated in FIGS. 3, 4, 5 and 6, the guard member 48 is a generally cylindrical member having one end 86 open to allow the guard member to move over the tip 42 of the needle element 40 and at its other end are the collar elements 62 and 64 which coact with the locking section 50 of the locking element 44 to permanently lock the guard member in position when it is moved forward. Internal rails 87 guide the guard member 48 as it moves forward. The collar elements 62 and 64 are formed in the upper end of the guard member 48 by a pair of teardrop shaped slits 88 which oppose one another and run laterally along the side wall of the guard member. The collar elements 62 and 64 form therebetween an open section, and each collar element includes a finger section 90 which wedges in to the annular recess 60 of the locking section 50. The teardrop slits 88 enable collar elements 62 and 64 to expand outwardly as the guard member 48 is moved forward. When the finger sections 90 are opposite the recess 60 they snap inwardly, moving from a flexed to a unflexed position allowing the finger sections to grasp and permanently lock guard member to the locking section 50.

OPERATION

To use the improved medical device 10 of this invention it is first removed from the housing 12 by detaching the cover 20 and then, while grasping the sheath 14, securing the device to a syringe (not shown). This is accomplished by grasping the sheath 14 and turning it so that the internal splines 25 engage the planar member 80 and cause the device 10 to rotate as the dog ears 74 are inserted into the syringe. The dog ears 74 will then grasp the locking elements on the syringe to secure the device 10 in position, whereupon, the sheath 14 is pulled off the device to expose the tip 42 of the needle element 40. A drug is added to the needle/syringe combination at this point. The user then inserts the needle element 40 into the patient, makes the injection, and then grasps the guard member 48, while withdrawing the needle element from the body of the patient. This moves the guard member 48 relative to the needle shaft so that the collar elements 62 and 64 slide over the locking section 50 and into the recess 60, permanently locking the guard member 48 in position to cover the tip 42 of the needle element 40. The device 10 may now be discarded.

Because of the construction of the locking element 44, the device of this invention is easy to mass produce and additionally provides extra safety so that the guard member 48 in the forward position will never move accidentally due to a failure of the bond between the locking element and the shaft of the needle element 44.

SCOPE OF THE INVENTION

The above description presents the best mode contemplated in carrying out the invention. This invention is, however, susceptible to modifications and alternate constructions from the embodiment shown in the drawing and described above. Consequently, it is not the intention to limit this invention to the particular embodiment disclosed. On the contrary, the intention is to cover all modifications and alternate constructions coming within the spirit and scope of the invention as generally expressed by the following claims.

We claim:

1. In an improved medical device including:
   (a) a needle having a hollow shaft terminating in an open tip adapted to penetrate the body of a patient;
   (b) a guard member on the shaft of the needle and movable axially along the shaft between a first position where the guard member is inwardly from the tip to expose said tip to enable it to penetrate the body of a patient and a second position where the guard member covers said tip to prevent needle sticks; and
   (c) locking means mounted along said needle shaft which permanently locks the guard member in the second position upon movement of said guard member from the first position to the second position,
      the improvement wherein the locking means has integral therewith and extending therefrom an elongated stem member made of a polymeric material through which a substantial portion of the needle shaft extends, said stem being bonded to the shaft during molding, with the stem being formed about the needle shaft by application of pressure to molten polymeric material which, upon cooling, shrinks and bonds to the surface of the shaft of the needle.

2. The improved device of claim 1 where the locking means and stem cover over 50% of the surface area of the exterior of the needle.

3. The improved medical device of claim 2 wherein a guard mounting means is formed at an end of the stem remote from the locking means.

4. The improved device of claim 3 wherein the guard mounting means includes a planar member and the guard member has a collar section divided by a lateral slit therein into which the planar member is received when the guard member is in the first position.

5. A medical device including:
   (a) an elongated, metal needle having a hollow shaft terminating in an open tip adapted to penetrate the body of a patient;
   (b) a guard member on the shaft of the needle and movable axially along the shaft between a first position where the guard member is inward from the tip to expose said tip to enable it to penetrate the body of a patient and a second position where the guard member covers said tip to prevent needle sticks, said guard member having at an end remote from said tip of the needle collar means adapted to flex outwardly under pressure and return to an unflexed condition upon release of pressure;
   (c) locking means mounted along said needle shaft including a recess into which the collar fits securely upon movement of said guard to the second position, said guard means permanently locking the guard member in the second position upon movement of said guard member from the first position to the second position;
   (d) an elongated stem member integral with the locking means and extending therefrom which is made of a polymeric material and through which a substantial portion of the needle shaft extends, said stem being bonded to the shaft during molding, with the stem being formed about the needle shaft by application of pressure to the molten polymeric material which, upon cooling, shrinks and bonds to the surface of the shaft of the needle; and
   (e) said locking means and stem covering at least 50% of the surface area of the exterior of the needle.

6. The improved medical device of claim 5 wherein a guard mounting means is formed at an end of the stem remote from the locking means.

7. The improved device of claim 5 wherein the guard mounting means includes a planar member and the collar means is divided by a lateral slit therein into which the planar member is received when the guard member is in the first position.

8. An improved medical device, comprising:
   a needle;
   a guard member axially movable relative to the needle in a distal direction from a first position in which the tip of the needle is exposed, to a second position in which the tip of the needle is covered to prevent needle sticks;
   a locking member mounted on the shaft of the needle which secures the guard in said second position, and
   said locking member including an elongated stem which is bonded to the needle shaft and covers a substantial portion of the surface area of the exterior of the needle to provide bonding of the stem to the needle.

9. A medical device, comprising:
   a hub for connection to a source of fluid medication;
   a hollow needle connected at one end to the hub and terminating at its other end in a pointed tip;
   a guard member moveable axially relative to the needle, from a first proximal position in which the tip of the needle is exposed, to a second distal position in which the tip of the needle is shielded by the guard to prevent needle sticks;
   a locking member disposed between the hub and the needle tip for interacting with the guard to retain the guard in the second position upon movement of the guard from the first position; and
   an elongate stem extending along the needle from the hub to the locking member for preventing axial movement of the locking member relative to the needle.

10. A medical device as in claim 9, wherein the hub, the elongate stem and the locking member comprise a unitary structure.

11. A medical device as in claim 10, wherein the stem is an elongated hollow cylindrical member molded integrally with the hub and the locking member.

12. A medical device as in claim 9, wherein the guard comprises a radially inwardly directed collar, and the locking member comprises at least one shoulder defining an annular recess for receiving the collar on the guard when the guard is in the second position to prevent axial movement thereof.

13. A medical device as in claim 10, wherein the stem is disposed coaxially about the needle and molded thereto to prevent movement of the stem along the needle.

14. A medical device as in claim 9, wherein the locking member comprises a ramp which extends radially outwardly in the distal direction.

15. A medical device as in claim 9, wherein the locking member comprises an annular conical portion, extending radially outwardly in a distal direction, and terminating in a rear shoulder defining the proximal boundary of an annular groove.

16. A medical device as in claim 9, further comprising a connector secured to the hub for releasably securing said needle in fluid communication with the delivery end of a syringe.

17. A medical device as in claim 16, wherein both of said first and second positions of said guard member are distal of the delivery end of said syringe.

18. A medical device as in claim 9, further comprising means for releasably retaining said guard in said first position.

* * * * *

UNITED STATES PATENT AND TRADEMARK OFFICE
CERTIFICATE OF CORRECTION

PATENT NO.   : 4,816,024
DATED        : March 28, 1989
INVENTOR(S)  : Dennis L. Sitar et al.

It is certified that error appears in the above-identified patent and that said Letters Patent is hereby corrected as shown below:

Column 4, line 5, change "4" to --46--

Abstract, line 6, change "portion an essentially" to
    --portion of the exterior--

Abstract, line 6, after "exterior" insert --surface of the needle shaft to provide an essentially--

Signed and Sealed this

Twelfth Day of February, 1991

*Attest:*

HARRY F. MANBECK, JR.

*Attesting Officer*    *Commissioner of Patents and Trademarks*